United States Patent
Bevz et al.

(10) Patent No.: US 11,089,784 B2
(45) Date of Patent: Aug. 17, 2021

(54) METHOD AND "IDEPS" COMPOSITION FOR DESTROYING MICROORGANISMS IN A SESSILE STATE

(71) Applicant: Ideps GmbH, Vienna (AT)

(72) Inventors: Serhei Vladymyrovych Bevz, Odessa (UA); Aleksandr Vasylevych Koval, Odessa (UA)

(73) Assignee: Ideps GmbH, Vienna (AT)

( * ) Notice: Subject to any disclaimer, the term of this patent is extended or adjusted under 35 U.S.C. 154(b) by 6 days.

(21) Appl. No.: 16/462,689

(22) PCT Filed: Dec. 19, 2016

(86) PCT No.: PCT/UA2016/000147
§ 371 (c)(1),
(2) Date: May 21, 2019

(87) PCT Pub. No.: WO2017/127040
PCT Pub. Date: Jul. 27, 2017

(65) Prior Publication Data
US 2020/0077661 A1   Mar. 12, 2020

(30) Foreign Application Priority Data

Nov. 28, 2016 (UA) .............................. a 2016 12062

(51) Int. Cl.
| | | |
|---|---|---|
| *A01N 59/02* | (2006.01) | |
| *A01N 33/12* | (2006.01) | |
| *A01N 43/84* | (2006.01) | |
| *A01N 31/02* | (2006.01) | |
| *A01N 59/16* | (2006.01) | |
| *A01N 37/04* | (2006.01) | |
| *A01N 33/04* | (2006.01) | |
| *A01N 41/04* | (2006.01) | |

(52) U.S. Cl.
CPC .............. *A01N 59/02* (2013.01); *A01N 31/02* (2013.01); *A01N 33/04* (2013.01); *A01N 33/12* (2013.01); *A01N 37/04* (2013.01); *A01N 41/04* (2013.01); *A01N 43/84* (2013.01); *A01N 59/16* (2013.01)

(58) Field of Classification Search
CPC ...................................................... A01N 59/02
See application file for complete search history.

(56) References Cited

U.S. PATENT DOCUMENTS

| | | | | |
|---|---|---|---|---|
| 2003/0079758 | A1* | 5/2003 | Siegel ............... | H01M 8/04089 134/3 |
| 2014/0294742 | A1* | 10/2014 | Fischer ................. | A61K 8/345 424/52 |
| 2016/0298060 | A1* | 10/2016 | Ludwig ............... | C11D 3/1213 |

FOREIGN PATENT DOCUMENTS

| | | |
|---|---|---|
| RU | 2408388 C1 | 1/2011 |
| RU | 2561053 C2 | 8/2015 |

\* cited by examiner

*Primary Examiner* — Sarah Alawadi
(74) *Attorney, Agent, or Firm* — Nadya Reingand; Yan Hunkin

(57) ABSTRACT

A composition for destroying microorganisms is used for destroying microflora (bacteria, protozoan fungi, etc.) in a sessile state (hereinafter, a biofilm). The composition can find its application in medicine, industry, agriculture and various technical fields for destroying biological films comprised of complex bacterial communities in an extracellular polymeric substance (an exopolymeric matrix), which form on different types of surfaces: biological, industrial, etc. The composition is pre-prepared by dissolving an oxidant and a buffer compound in a solvent. Once the composition has been prepared, it is applied to a biofilm on the surface of an object.

1 Claim, 1 Drawing Sheet

METHOD AND "IDEPS" COMPOSITION FOR DESTROYING MICROORGANISMS IN A SESSILE STATE

CROSS-REFERENCE TO RELATED APPLICATIONS

The present patent application is a National stage application of PCT application PCT/UA2016/000147 filed on Dec. 19, 2016, which claims priority to Ukranian patent application UA a201612062 filed Nov. 28, 2016.

FIELD OF INVENTION

The invention relates to the field of microflora destruction technologies (bacteria, protozoan fungi, etc.), namely microorganisms in sessile state (hereinafter—biofilm), and can be used in medicine, industry, agriculture and various fields of technology for the destruction of biological films which are highly organized communities of bacteria in the extracellular polymeric substance (hereinafter referred to as the exopolymer matrix) formed on surfaces of different origin (biological, industrial, etc.).

BACKGROUND

From the current level of technology, which relates to the area under consideration, the closest, by the combination of features, to the claimed invention is a method of killing microorganisms in a sessile state, which involves contact of a biofilm (formed within 24 hours), in an exopolymer matrix of which there are coagulase-negative staphylococci, with an active substance that inhibits the activity of that bacteria, where a low molecular weight cationic peptide—varnerin is used the active substance at a concentration of varnerin of 16-128 µg/ml for 10 µg of biofilm, with subsequent incubation at 37° C. for 24 hours, which leads to partial destruction of the exopolymeric matrix due to the activation of autolytic systems of bacterial cells affected by varnerin (up to 30% of bacterial cells die in 24 hours) (V. P. Korobov, L. M. Lemkina, L. B. Filatova, T V Polyudova The destruction of biofilms of coagulase-negative staphylococci with cationic peptide varnerin. Proceedings of the Samara Scientific Center of the Russian Academy of Sciences 2011, vol. 13, no. 5 (3), pp. 156-159).

The claimed invention coincides with the known method of destroying microorganisms in the sessile state according to the following essential features: by contacting the microbial biofilm with the active substance.

However, the known method of killing microorganisms in a sessile state does not provide the technical result of the claimed invention, which is due to the operations performed by the method and the active substance used—varnerin, which is used in the method, and acting directly on microorganisms that, under conditions of biofilm, i.e. in sessile state, are difficult to access for varnerin, since the biofilm itself has a complex composition and is formed (up to 75%) from polysaccharides (cellulose, pectin, curdlan, dextran, levan, etc.), and its composition changes over time, which makes it difficult for the penetration of varnerin into microorganisms, and the destruction of the biofilm itself is secondary, as varnerin does not directly destroy the exopolymer matrix of the biofilm, the destruction of which is due to the activation of autolytic systems of cells attacked by varnerin, and as the result is the efficiency of this method, which does not completely eliminate even the "young" biofilm (24 hours old) and the bacteria in it (up to 70%), when it mainly consists of mono and oligosaccharides, and to a lesser extent polysaccharides, and thus, cannot be used for practical solutions for the destruction of biofilms.

SUMMARY

The problem to which the invention is directed is to improve the known method of destroying microorganisms in the sessile state by replacing the active substance with the one that will ensure the primary destruction of the exopolymeric matrix of the biofilm. It will initially transfer microorganisms from the sessile state to a planktonic form and at the same time affect the microorganisms themselves, which allows for the effective destruction of biofilms of various microbial origin, of different age and without changing the state of the surface on which it is fixed.

The task is solved in the method of destruction of microorganisms in sessile state, carried out by contact of the exopolymeric matrix of the biofilm with the active substance, so that according to the subject invention, the microorganisms are first transferred to the planktonic state by dissolving the biofilm matrix, and as the active substance they use an oxidant solution and a blocking agent OH-groups. This set of essential features provides a technical result, consisting in the fact that the proposed method primarily provides for the destruction of the exopolymeric matrix of a microbial biofilm, i.e. transfers microorganisms from sessile state to planktonic form, which itself leads to the weakening of microorganisms; and directly affects the microorganisms, regardless of their nature (bacteria, fungi, etc.) and the age of the biofilm.

From the current level of technology, which belongs to the considered area, the closest, by the combination of features, to the claimed invention, is the composition for the destruction of microorganisms in sessile state, which is an aqueous solution of the active substance, which is used as a low molecular weight cationic peptide—vararin at a concentration of 16-128 µg/ml per 10 µg of biofilm, and the contact of the solution with the biofilm (formed within 24 hours) is carried out by incubation at 37° C. for 24 hours that provides partial destruction of the biofilm exopolymeric matrix due to the secondary action of varnerin—activation of autolytic systems of bacterial cells affected by varnerin (up to 30% of bacterial cells die within 24 hours) (V. P. Korobov, L. M. Lemkina, L B. Filatova, T V Polyudova The destruction of biofilms of coagulase-negative staphylococci with cationic peptide varnerin. Proceedings of the Samara Scientific Center of the Russian Academy of Sciences 2011, vol. 13, no. 5 (3), pp. 156-159).

The claimed invention coincides with the known composition for the destruction of microorganisms in the sessile state, according to the following set of essential features: it contains the active substance and the solvent.

However, the known composition for the destruction of microorganisms in sessile state does not provide the technical result of the claimed invention, which is due to the components, namely the use of the active ingredient varnerin, which is used in the composition, and acting directly on the microorganisms that, under biofilm conditions, are in the sessile phase, i.e. are difficult to access for varnerin, since the biofilm itself has a complex composition and is formed (up to 75%) from polysaccharides (cellulose, pectin, curdlan, dextran, levan, etc.), and its composition changes over time, which makes it difficult for varnerin to penetrate microorganisms, and the destruction of the biofilm itself is of a secondary nature, since varnerin does not directly destroy the exopolymer matrix of the biofilm, the destruction of which is due to the activation of autolytic systems of cells attacked by varnerin, and as a result, the method has low efficiency. This composition does not completely eliminate even the "young" biofilm (24 hours old) and the bacteria in it (up to 70%), when it mainly consists of mono and oligosaccharides, and to a lesser extent polysaccharides, and cannot be used for practical solutions to the destruction of biofilms for domestic or industrial purposes.

The problem to which the invention is directed to is to improve the known composition for the destruction of microorganisms in the sessile state by changing its qualitative and quantitative composition, which will ensure the primary destruction of the exopolymeric matrix of the biofilm. Primarily, it will ensure the transfer of microorganisms from the sessile state to the planktonic form and simultaneously affect the microorganisms themselves, which allows the effective destruction of biofilms of various microbial origin, of different ages, without changing the state of the surface on which it is fixed.

The task is solved in the composition for the destruction of microorganisms in sessile state containing the active substance and the solvent with the fact that according to the subject invention, as the active substance an oxidizer solution and a substance that blocks OH-groups are used.

This set of essential features provides the technical result, consisting in the fact that the proposed composition provides primarily the destruction of the exopolymeric matrix of a microbial biofilm, i.e. transfers microorganisms from sessile state to planktonic form, which itself leads to the weakening of microorganisms; and directly affects the microorganisms, regardless of their nature (bacteria, protozoan fungi, etc.) and the age of the biofilm, which leads to the complete destruction of both the biofilm and the bacteria forming it.

Additional technical result, which consists in increasing the efficiency of the process of killing microorganisms and expanding the range of chemicals depending on the properties of the surfaces that are processed, is ensured by using sodium peroxydisulfate as an oxidizing agent, and sodium hydroxide as a blocking OH group, and water as a solvent, having in mass. %:
Sodium peroxydisulfate not less than 0.5
Sodium hydroxide not less than 0.5
The remainder being water.

The proportion of components is due to the following: when going below the lower values of the components, the destruction of the biofilm does not occur, and the choice of the upper limit of the content of the components due to their solubility.

An additional technical result consisting in increasing the efficiency of the process of destroying microorganisms and expanding the range of chemicals depending on the properties of the surfaces being treated is ensured by using potassium nitrite as an oxidizing agent, and benzyltrimethylammonium hydroxide is used as an OH blocking agent, and water as a solvent, with the following content of the components, mass. %:
Potassium nitrite not less than 0.5
Benzyltrimethylammonium hydroxide not less than 0.5
The remainder being water.

The proportion of the components is due to the following: when going below the lower values of the components, the destruction of the biofilm does not occur, and the choice of the upper limit of the content of the components due to their solubility.

Additional technical result, which consists in increasing the efficiency of the process of killing microorganisms and expanding the range of chemical substances depending on the properties of the surfaces that are processed, is ensured by using N-methylmorpholine N-oxide as an oxidizing agent, and potassium tert-butoxide as an OH blocking agent, and dimethyl sulfoxide as a solvent, with the following proportion of the components, mass. %:
N-oxide N-methylmorpholine not less than 0.5
Potassium tert-butylate not less than 0.5
The solvent is the rest.

The proportion of the components is due to the following: when going below the lower values of the components, the destruction of the biofilm does not occur, and the choice of the upper limit of the content of the components due to their solubility.

An additional technical result consisting in increasing the efficiency of the process of killing microorganisms and expanding the range of chemicals depending on the properties of the surfaces being treated is ensured by using potassium hexacyanoferrate as an oxidizing agent, potassium hydroxide as an OH-blocking agent and water as a solvent, with the following components, mass. %:
Potassium hexacyanoferrate not less than 0.5
Potassium hydroxide not less than 0.5
The remainder being water.

The proportion of the components is due to the following: when going below the lower values of the components, the destruction of the biofilm does not occur, and the choice of the upper limit of the content of the components due to their solubility.

Additional technical result, which consists in increasing the efficiency of the process of destruction of microorganisms and expanding the range of chemical substances depending on the properties of the surfaces that are processed, is ensured by using ammonium cerium (IV) nitrate as an oxidizing agent, formic acid as a blocking OH group, and water as a solvent, with the following proportion of the components, mass. %:
Ammonium cerium (IV) nitrate not less than 0.5
Formic acid not less than 0.5
The remainder being water.

The proportion of the components is due to the following: when going below the lower values of the components, the destruction of the biofilm does not occur, and the choice of the upper limit of the content of the components due to their solubility.

An additional technical result consisting in increasing the efficiency of the process of killing microorganisms and expanding the range of chemicals depending on the properties of the surfaces that are processed is ensured by using sodium bromate as an oxidizing agent, sodium hydroxide as an OH blocking substance, and water as a solvent, with the following proportion of the components, mass. %:
Sodium bromate not less than 0.5
Sodium hydroxide not less than 0.5
The remainder being water.

The proportion of the components due to the following: when going below the lower values of the components, the destruction of the biofilm does not occur, and the choice of the upper limit of the content of the components due to their solubility.

Additional technical result, which consists in increasing the efficiency of the process of killing microorganisms and expanding the range of chemicals depending on the properties of the surfaces that are processed, is ensured by using sodium dichromate as an oxidizing agent, acetic acid as an OH-blocking agent, and dimethyl sulfoxide as a solvent, with the following components, mass. %:
Sodium dichromate at least 0.5

Acetic acid not less than 0.5
The solvent is the rest.

The proportion of the components is due to the following: when going below the lower values of the components, the destruction of the biofilm does not occur, and the choice of the upper limit of the content of the components due to their solubility.

Additional technical result consisting in increasing the efficiency of the process of destruction of microorganisms and expanding the range of chemicals depending on the properties of the surfaces that are processed is ensured by using tetraalkylammonium chloride as an oxidizing agent, methylsulfonic acid as an OH blocking substance, and dimethyl sulfoxide as a solvent, with the following components, mass. %:
Tetraalkylammonium chloride at least 1.0
Methylsulfonic acid at least 0.5
The solvent is the rest.

The proportion of the components is due to the following: when going below the lower values of the components, the destruction of the biofilm does not occur, and the choice of the upper limit of the content of the components due to their solubility.

An additional technical result consisting in increasing the efficiency of the process of killing microorganisms and expanding the range of chemicals depending on the properties of the surfaces that are processed is ensured by using dinitrogen tetroxide as the oxidant, Citric acid as an OH blocking substance, and dimethyl sulfoxide as a solvent, with the following components, mass. %:
Dinitrogen tetroxide not less than 0.5
Citric acid not less than 0.5
The solvent is the rest.

The proportion of the components is due to the following: when going below the lower values of the components, the destruction of the biofilm does not occur, and the choice of the upper limit of the content of the components due to their solubility.

Additional technical result consisting in increasing the efficiency of the process of killing microorganisms and expanding the range of chemicals depending on the properties of the surfaces that are processed is ensured by the use of diethylamine as an oxidant, sulfur dioxide as a blocking substance, and dimethyl sulfoxide as a solvent, with the following components, mass. %:
Diethylamine not less than 4.5
Sulfur dioxide not less than 1.5
The solvent is the rest.

The proportion of the components is due to the following: when going below the lower values of the components, the destruction of the biofilm does not occur, and the choice of the upper limit of the content of the components due to their solubility.

Additional technical result, consisting in preventing the destruction of the surface on which the biofilm is located, is ensured by the fact that the composition additionally contains a corrosion inhibitor (hereinafter the inhibitor).

An additional technical result consisting in eliminating the reaction of the oxidizing agent with the reactive hydroxyl groups of the exopolymeric matrix polysaccharides (at a pH of <10.50) is ensured by the fact that the composition additionally contains a reagent that protects hydroxyl groups (hereinafter the protective reagent).

DETAILED DESCRIPTION OF THE PREFERRED EMBODIMENT

Figure 1:
FIG. 1 is a photographic image of a biofilm prior to use of the composition of the invention (magnification 300 times)
Figure 2:
FIG. 2—photographic image of a biofilm in 5 minutes. after using the composition of the invention (an increase of 300 times)
Figure 3:
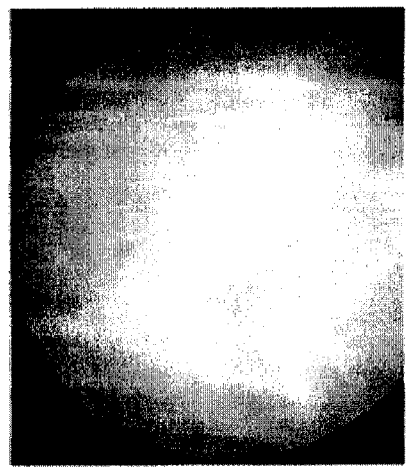
FIG. 3—photographic image of a biofilm in 10 minutes. after using the composition of the invention (an increase of 300 times)

The proposed method and composition for the destruction of microorganisms in sessile state is as follows.

Pre-prepare the composition for the destruction of microorganisms in sessile state, for which dissolve the oxidizing agent and the substance that blocks the OH-group in a solvent which is chosen depending on the chemical nature of the dissolved components of the composition. As an oxidizing agent, any inorganic or organic substance or compound exhibiting oxidative properties is used, and as a substance that blocks OH groups, any inorganic or organic substance or compound is used that enhances the oxidative reactivity (oxidative) ability, which blocks the chemical reactions of the used oxidant with hydroxyl groups of polysaccharides exopolymer matrix, while maintaining the pH level of the composition. The components from which the composition is prepared for the destruction of microorganisms in sessile state, can be used, for example: an aqueous solution of sodium peroxydisulfate in the amount of 0.50-35.70 wt. %. and sodium hydroxide in the amount of 0.50-40.00 wt. %; an aqueous solution of potassium nitrite in the amount of 0.50-75.70 wt. % and benzyltrimethylammonium hydroxide in the amount of 0.50-40.00 wt. %; N-methylmorpholine N-oxide in the amount of 0.50-50.00 wt. % and potassium tert-butoxide in the amount of 0.50-35.00 wt. % In dimethyl sulfoxide; an aqueous solution of potassium hexacyanoferrate in the amount of 0.50-31.65 wt. % and potassium hydroxide in the amount of 0.50-54.10 wt. %; ammonium cerium (IV) nitrate aqueous solution in the amount of 0.50-58.50 wt. % and formic acid in the amount of 0.50-85.00 wt. %; an aqueous solution of sodium bromate in the amount of 0.50-28.50 wt. % and sodium hydroxide in the amount of 0.50-40.00 wt. %; a solution of sodium dichromate in the amount of 0.50-30.00 wt. % and acetic acid in the amount of 0.50-80.00 wt. % in dimethyl sulfoxide; a solution of tetraalkylammonium chloride in the amount of 1.0-70.00 wt. % and methylsulfonic acid in the amount of 0.50-75.00 wt. % in dimethyl sulfoxide; a solution of dinitrogen tetraoxide in the amount of 0.50-35.00 wt. % and citric acid in the amount of 0.50-80.00 wt. % in dimethyl sulfoxide; a solution of diethylamine in the amount of 4.50-45.00 wt. % and sulfur dioxide in the amount of 1.50-25.00 wt. % in dimethyl sulfoxide, as well as other similar systems containing organic and inorganic oxidizers and substances that block —OH group.

The choice of the quantitative content of the components is due to the following:

The minimum proportion of the components ensure the achievement of the technical result—the destruction of the biofilm matrix and the transfer of microorganisms from the sessile to the plankton form. If the amount is less than the lower value, the destruction of the exopolymer matrix does not occur, i.e. the technical result is not achieved, and the destruction of microorganisms occurs inside the exopolymer matrix, which increases the duration of the process and increases the consumption of the composition. The upper values of the components are due to their solubility limit in the solvent.

In the case when the composition for the destruction of microorganisms in the sessile state has a pH value of <10.50, then a protective reagent is added to it—a compound to protect the hydroxyl groups of the polysaccharides of the exopolymeric matrix, which can be any of the compounds used for these purposes: iodomethane, benzyl chloride, allyl bromide, triethylsilane, dimethyl sulfate, benzyl bromide, trichloroacetyl chloride, etc. in an amount of 0.01-5.00 wt. %.

If the composition for the destruction of microorganisms is also aggressive for the material of the object on which the biofilm is located, for example, metal surfaces, then a corrosion inhibitor is added to the composition, which can be any of the substances used for these purposes, for example: sodium N, N-diethyldithiocarbamic acid, dextrin, 3-methoxy-4-propargyloxy-benzoic aldehyde, sodium sulfur, methyl ethyl ketone, diisopropylammonium nitrite, etc. in an amount of 0.05-5.00 wt. %.

After preparation of the composition for the destruction of microorganisms in sessile state, it is deposited on the object, the surface of which contains a biofilm.

As such an object, a plastic tray is used, on which biofilm was previously grown in the period from January 2016 to September 2016 by continuously supplying water taken from a natural reservoir. During this period, a well-visible layer of an adhesion biofilm formed by bacteria previously found in water is formed on the surface of the tray in contact with the running water: *Escherichia coli, Enterococcus faecalis, Enterobacter cloacae*.

The composition for the destruction of microorganisms in sessile state poured into the tray. When using the composition with the content of components corresponding to the lower value of the range, the complete destruction of the exopolymeric matrix of the biofilm occurs within no more than 3 hours, while simultaneously destroying the bacteria, which, as a result of the destruction of the matrix, change from sessile form to planktonic, where the effectiveness of the biocidal properties of the proposed composition is significantly better. The test show that the bacteria *Escherichia coli, Enterococcus faecalis, Enterobacter cloacae* did not give positive results, indicating their complete destruction.

DETAILED DESCRIPTION OF THE PREFERRED EMBODIMENT

The proposed method and composition for the destruction of microorganisms in sessile state is as follows.

Pre-prepare the composition for the destruction of microorganisms in sessile state, for which dissolve the oxidizing agent and the substance that blocks the OH-group, in a solvent. An aqueous solution of sodium peroxydisulfate at a concentration of 10.00 wt. % and sodium hydroxide at a concentration of 15.00 wt. % is used as components from which the composition is prepared for the destruction of microorganisms in the sessile state. Since the pH of the composition is greater than 10.50, no protective reagent is added.

After preparation of the composition for the destruction of microorganisms in sessile state, it is deposited onto the object, the surface of which contains a biofilm.

As a treatment object containing a biofilm, the root canal of the 31st tooth was used in the treatment of chronic periodontitis with a biofilm, which was formed naturally by microorganisms characteristic of dental root canals, such as: *Enterococcus faecalis, Candida albicans, Streptococcus oralis, Streptococcus mitis, Escherichia coli*.

As a result of the introduction of the claimed composition for the destruction of microorganisms in the sessile state and its exposure for 10 minutes, the quantitative indicator of the enzyme urease of the material from the root canal was 0.00 μkat/l, which indicates that a complete destruction (dissolution) of the exopolymeric biofilm matrix occurred and bacteria that have passed into the plankton form are completely destroyed by the bactericidal action of the claimed composition.

INDUSTRIAL APPLICABILITY

The invention can be implemented in conditions of industrial production and used for domestic, industrial and medical purposes.

What is claimed is:
1. A method for the destruction of microorganisms in a sessile state, comprising:
    exposing a microbial biofilm to an aqueous solution consisting of an antiseptic and a solvent,
    said aqueous solution transforming said microbial biofilm from a sessile state to a planktonic form and causing a dissolution of said microbial biofilm,
    wherein said antiseptic is a mixture of:
        sodium peroxydisulfate in an amount of at least 0.50 wt. %, and
        sodium hydroxide in an amount of at least 0.50 wt. %, and
    wherein said solvent is water in an amount of remaining wt. %.

* * * * *